United States Patent [19]
Hanlon

[11] Patent Number: 5,201,418
[45] Date of Patent: Apr. 13, 1993

[54] NEEDLE DISPOSAL SYSTEM

[76] Inventor: Ronnie Hanlon, 5307 E. 33 St., Tulsa, Okla. 74135

[21] Appl. No.: 921,454

[22] Filed: Jul. 28, 1992

Related U.S. Application Data

[63] Continuation of Ser. No. 746,776, Aug. 16, 1991, abandoned.

[51] Int. Cl.$^5$ .............................................. B65D 83/02
[52] U.S. Cl. .................................... 206/366; 220/351; 220/379; 220/908; 232/43.1; 232/44
[58] Field of Search ............... 206/365, 366, 370, 557; 220/229, 351, 379, 908; 232/44, 48, 43.1

[56] References Cited

U.S. PATENT DOCUMENTS

| | | | |
|---|---|---|---|
| 614,058 | 11/1898 | Moreno et al. | 232/48 |
| 2,597,460 | 5/1952 | Everhardt | 206/557 X |
| 3,876,067 | 4/1975 | Schwarz | 206/366 X |
| 4,380,292 | 4/1983 | Cramer | 206/366 |
| 4,485,918 | 12/1984 | Mayer | 206/366 |
| 4,603,791 | 8/1986 | Spierer et al. | 232/44 X |
| 4,679,700 | 7/1987 | Tharrington et al. | 220/229 X |
| 4,715,498 | 12/1987 | Henifl | 206/366 |
| 4,722,472 | 2/1988 | Bruno | 206/366 X |
| 4,753,386 | 6/1988 | Phihon, Sr. | 232/43.1 |
| 4,804,090 | 2/1989 | Schuh et al. | 206/366 |
| 4,809,850 | 3/1989 | Laible et al. | 220/908 X |
| 4,848,569 | 7/1989 | Leishman | 206/365 |
| 4,875,583 | 10/1989 | Nosanchuk | 220/908 X |
| 4,890,734 | 1/1990 | Gach | 206/366 |
| 4,919,264 | 4/1990 | Shinall | 206/366 X |
| 4,969,554 | 11/1990 | Sawaya | 206/366 X |
| 5,046,614 | 9/1991 | Tomes et al. | 206/366 |
| 5,047,019 | 9/1991 | Sincock | 206/366 X |

FOREIGN PATENT DOCUMENTS

682465  3/1964  Canada ................................. 220/908

Primary Examiner—Bryon P. Gehman
Attorney, Agent, or Firm—Robert E. Massa

[57] ABSTRACT

A system for safely and conveniently disposing of contaminated hypodermic needles comprises a disposal container for accumulating contaminated hypodermic needles which had been disposed therein after having been initially collected within a tray containing a supply of needle-retaining material. The needle-retaining material is a soft material, similar to art gum eraser material, which is soft enough for a needle to penetrate yet sticky enough to retain the needle when he needle is released from the syringe. The tray comprises a base, a pair of side walls, a handle extending from one side wall for easy transport of the tray, and the supply of needle-retaining material. The needle-retaining material in the tray may be presented in two different forms, either as a contiguous supply of strips in the tray or as individual small cup-like depressions each containing a small amount. For a contiguous supply, the needle-retaining material may be formed of adjoining strips so that a strip may be removed when sufficiently filled with needles. Individual cup-like depressions should have tapered walls so that each cup of material may be easily removed. The cups may be either conical or pyramidal in configuration. The disposal container is adapted to be fitted with a slide-on funnel member having a pair of spring-biased doors openable downwardly into the disposal container. Preferably, the spring-biased doors are openable with the weight of a needle component placed thereon. A slide-on top cover is adapted to be held in temporary position on the bottom of the disposal container until needed to replace the funnel member to close the container for disposal.

5 Claims, 5 Drawing Sheets

NEEDLE DISPOSAL SYSTEM

This is a continuation of copending application Ser. No. 0746,776 filed on Aug. 16, 1991, now abandoned.

FIELD OF THE INVENTION

My invention relates to medical equipment. More particularly, my invention relates to medical equipment devoted to the collection and disposal of used hypodermic needles. Still more particularly, my invention relates to disposal systems for sharp-pointed and sharp-edged medical equipment, including hypodermic needles and syringes which have been contaminated through use. Still more particularly, my invention relates to medical disposal systems which provide means for safely collecting, transporting, and disposing of contaminated used medical instruments.

BACKGROUND OF THE INVENTION

Through the years the advancements in medical knowledge and treatment of illnesses has likewise brought about tremendous increase sin the use of various types of hypodermic needles, either for inoculations, transfusions, or blood sampling.

It is quite clear the hypodermic needles are very often associated with some form of disease or illness present in the blood system of a patient, for example, and as a result, the needles are then contaminated with infectious material. An inadvertent penetration of the skin of the medical technician handling the medical equipment would then very easily result in a serious infection with the same disease for which the patient is being treated.

The danger in handling contaminated, or potentially contaminated, medical equipment has been recognized for many years, and many attempts have been made to eliminate such danger completely, and provide people in the medical professions with safe means for handling any contaminated equipment.

Not only are medical technicians exposed to danger in handling hypodermic needles, but other familiar medical instruments, such as various kinds of scalpels, are commonly contaminated, and must be handled very carefully. Generically, in the medical profession, all of the sharp medical instruments, are referred to as "sharps".

For use, the medical technician handles the "sharp" with one hand, there is customarily no need to grasp a hypodermic syringe or a scalpel with both hands. Then, in disposing of the needle or scalpel, it is most often considered safest to construct a disposal system in which the "sharp" need be manipulated with only one hand while being discarded. Otherwise, for example, in disposing of a hypodermic needle, the syringe might be held in one hand while the needle is being removed from a non-disposable syringe with the other hand; or, a disposable needle and syringe, or scalpel, might be held in one hand while a disposal container is held open with the other hand.

Thus, preferably, the hand not needed for any assistance during disposal should be completely out of the way to avoid accidental contamination.

The prior art reveals different forms of disposal systems for "sharps", among which are the following U.S. Pat. Nos. which I had found:

| U.S. Pat. No. 3,876,067 | Schwarz | April 8, 1975 |
|---|---|---|
| U.S. Pat. No. 4,380,292 | Cramer | April 19, 1983 |
| U.S. Pat. No. 4,804,090 | Schuh et al | Feb. 14, 1989 |
| U.S. Pat. No. 4,848,569 | Leishman | July 18, 1989 |
| U.S. Pat. No. 4,890,734 | Gach | Jan. 2, 1990 |
| U.S. Pat. No. 4,919,264 | Shinall | April 24, 1990 |

U.S. Pat. No. 3,876,067 to Schwarz describes a collection box for syringe needles after use. The box contains a filling of disinfectant material. The upper portion is provided with a multiplicity of openings. For disposal a syringe is pressed slightly through one of the openings so that a head of the needle is deformed enough to pass through an opening and is caught behind a wall of an opening. The syringe may then be pulled loose of the needle.

U.S. Pat. No. 4,380,292 to Cramer describes a needle receptable which includes a base supporting an outer case in which a foam block rests. A contaminated needle is injected into the foam block, and when sufficient needles are injected into the foam block, the block is removed from the case and disposed of.

U.S. Pat. No. 4,804,090 to Schuh et al describes a disposal system for contaminated instruments comprising a device for transporting the instruments to a disposal container, The transporting device comprises a small cup with a grid-like cover. The cup is partially filled with styrofoam material into which used needles are inserted. The disposal container is a large receptacle having a paddle wheel mounted in the lid beneath a hinged door through which needles are drooped onto he paddle wheel. the paddle wheel is rotated so that the needles fall into the container.

U.S. Pat. No. 4,848,569 to Leishman describes a disposal apparatus for contaminated needles comprising a magazine structure provided with a plurality of small shield components. A lengthwise channel provides access to each shield. After use, a contaminated needle is inserted into the uppermost shield and the shield and the shield is removed form the magazine for further disposal.

U.S. Pat. No. 4,890,734 to Gach describes a disposable holder which includes a plurality of retaining orifices and a plurality of disposal orifices. Initially, a needle capped in its sheath is inserted into a retaining orifice. The needle is removed from its sheath for use leaving the sheath in he retaining orifice. After use, a needle and sheath may be removed from the retaining orifice and inserted into a disposal orifice for disposal into the storage location. The storage holder and the contents may be disposed of entirely.

U.S. Pat. No. 4,919,264 to Shinall describes a medical needle removing and disposing system comprising a box having a plurality of tubular chambers. Each tubular chamber contains a plastic substance such as a flower clay into which a used needle is inserted. The upper end of each tubular chamber has a specialized shape designed to assist in removing the needle from the sheath.

SUMMARY OF THE INVENTION

The primary object of my invention is to provide a disposal system for safely, conveniently, and efficiently collecting contaminated medical coinstruments.

Another object of my invention is to provide a disposal system for the collection of contaminated hypodermic needles in a manner permitting the instruments to be disposed of with minimal handling.

Still another object of my invention is to provide a disposal device for contaminated needles constructed in a manner to permit deposit of a needle by manipulation of only a syringe-bearing hand.

Still another object of my invention is to provide a disposal device designed for safely accumulating contaminated needles or other sharps.

Still another object of my invention is to provide a disposal apparatus into which contaminated instruments may be loaded by manipulation of one instrument-bearing hand of a medical technician, allowing the technician's other hand to remain safely out of imminent danger.

I have developed my disposal system for contaminated hypodermic needles as a simple and convenient system of protecting medical technicians from the usually serious consequences of accidental needle pricks or scrapes from other sharp instruments.

I felt that there need be a safe means for protecting the needle point, or other sharp point, from the time the needle has been used and contaminated until the needle has been collected and stored for ultimate disposal.

Obviously, after the medical technician has completed a vaccination, or other treatment with another form of sharp instrument, the greatest potential danger is to the fee hand of the technician, rather than the hand still holding the needle or other sharp instrument.

Therefore, I have designed my collection and accumulation system for contaminated needles to permit the medical technician to remove the needle from eh syringe and dispose of the needle while holding the syringe with one hand and keeping the other hand away from the needle or sharp instrument. My system is simple and may easily be operable with one hand, the hand holding the instrument, since the other hand is onto needed in order to hold any of the needle receiving components while the needle is being transported from the patient to the disposal equipment.

Even if the medical technician hold feed that the or she should require two hands to remove a needle from the syringe, that is, one hand holding the syringe and the other hand loosening the needle from the syringe, then the needle is still protected because the technician has already injected the needle, with one hand, into a cube or plug or disposable material, such as art gum, a material similar to eraser rubber, or some similar gelatinous, sticky material The needle is safely and securely in this disposable material. The needle could be disconnected from the syringe with the technician's other hand. The needle point is safely buried int eh receptive material and constitutes no threat of penetrating contamination to the hands of the technician.

I have provided several different configurations for the disposable material of my invention which I describe later.

For instance, I have arranged for the cubes or plugs of disposable material to be positioned in trays which include a plurality of small depressions or cube-like holders, each of which is filled with a sufficient amount of needle-retaining. These depressions or cups should be of proper configuration to permit the disposable material to be easily individually removed from eh tray for disposal, as desired, as when an individual cup is determined to have a sufficient number of contaminated needles inserted therein.

I have determined that the geometric design of the cup-like depressions must be of proper configuration to permit the needle-retaining material to be easily removed from the tray. The configuration must be at least of cylindrical or cubical shape, and preferably of conical or pyramidal shape, for example, in a manner that the smaller cross-sectional area of the needle-retaining depression should be at the bottom of the depression, thus, the needle-retaining material is formed with slanted walls and can be much more easily removed from the tray.

I display needle-retaining material units having conical and pyramidal shapes, but other configurations providing suitably slanted wall portions to permit easy removal o the units are also considered included.

The individual needle-retaining units could be removed from the tray merely by grasping and pulling upon an inserted needle or by waiting until all of the needle-retaining units are properly filled with needles and then dumping the entire tray contents upon and within a funnel member positioned upon the disposal container.

With my system needles are place din the safety of the needle-retaining material immediately after removal from a body portion of the patient. The needles may then be safely and conveniently transported to the disposal container within which they may accumulate until the technician finds it feasible or suitable to dispose of the contaminated needles and the disposal container.

Another configuration Id display for the needle-retaining material is to arrange the needle-retaining material in thick, wide strips in the bottom of a tray. I place these strips in contiguous arrangement so that a greater number of contaminated needles may be collected in a strip of material before the strip need be disposed of then is necessary with each of the cubes or plugs of material. Also, in this variation the entire tray would be covered with needle-retaining material so that a technician trying to insert a contaminated needle in the needle-retaining material would not have to devote particular attention to seeking an individual cube while he or she is also tending a patient. This arrangement is most helpful in a triage unit or psychiatric ward where the patient behavior could be erratic or unpredictable.

For disposal of a strip of needle-retaining material from a contiguous position on a tray, when the technician decides that a strip should be disposed of, here she merely removes an entire strip of needle-retaining material from the tray and diposes of it in the disposal container.

IN defining two operating steps involved in carrying out the method of my disposal system, I prefer to apply the term "collect" to the steps involved inserting the contaminated needles into the needle-retaining material and the term "accumulate" to he step of gathering and building a supply of contaminated needles within the disposal container.

I have designed the funnel member of the disposal container to be constructed to slide onto the disposal container so that it may be easily positioned thereon and easily removed when desired. I have also conceived that the funnel member for the disposal container and the tray components for the needle-retaining material could be of either reusable or disposable material.

IN disposable of the disposal container when it si decided that is contains sufficient contaminated needles, I provide that the funnel member ne removed from the container and a disposable slide-on cover be placed in position upon the container so that the entire device and contents may be properly disposed of according o the proper procedure of the organization where the contaminated needles are collected.

The above objects and advantages of my invention will become apparatus from my description of the following preferred embodiments of my invention.

DESCRIPTION OF THE PREFERRED EMBODIMENTS

Figure 1:
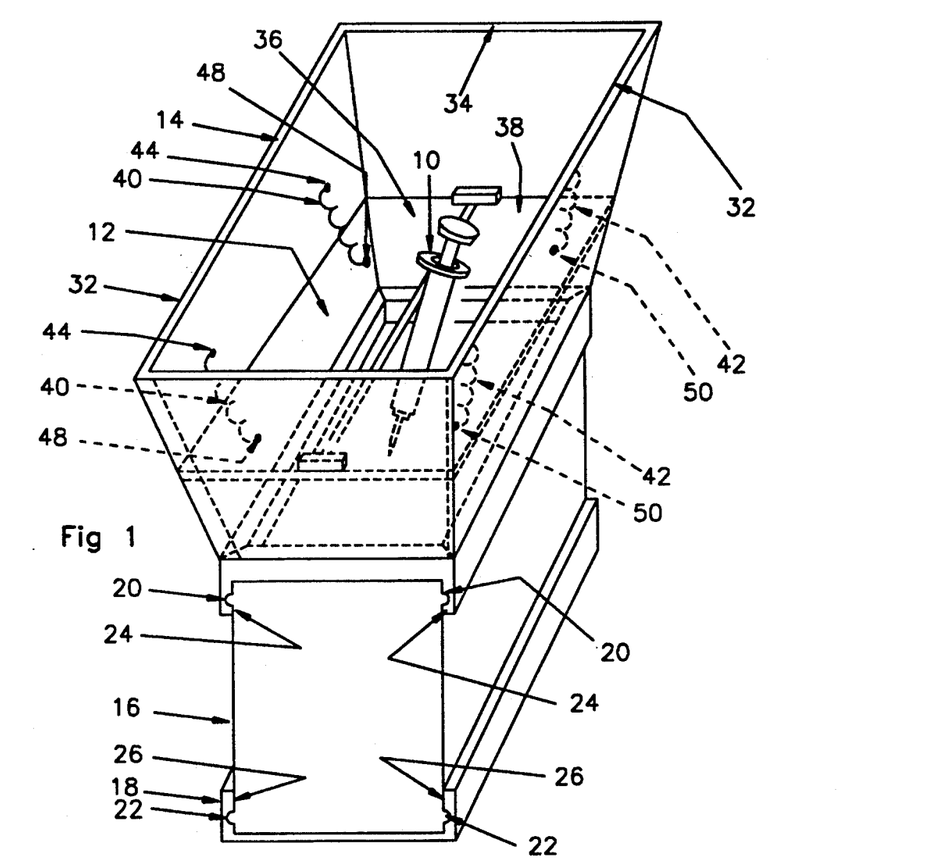
FIG. 1 is a perspective view of one embodiment of a needle disposing component according to my invention.
Figure 7:
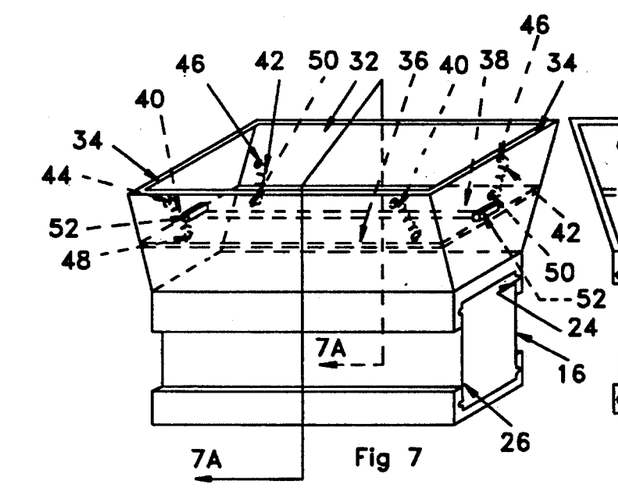
FIG. 7 is a side perspective view o the needle disposing component shown in FIG. 1.
Figure 7A:
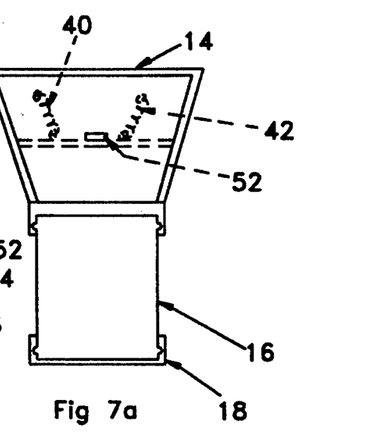
FIG. 7a is an end view of the needle disposing component along the lines 7a—7a of FIG. 7.

FIG. 1 describes one embodiment of a needle disposing system according to my invention showing a hypodermic syringe instrument 10, generally, in the process of being disposed upon a spring-biased door system 12, generally, of a funnel member 14, generally positioned upon a disposal container 16, generally, of my system. For further clarity, I show similar views by side perspective view of FIG. 7 and end view of FIG. 7a.

Essentially, the disposal container 16, generally, comprises a box-lid container provided with means for sliding attachment of funnel member 14, generally, and for a top cover 18, generally. Along two parallel sides of the disposal container 16, I have arranged small ridges 20 and 22 which match and cooperate with flanges 24 on the funnel member 14 and flanges 26 on the top cover 18.

The upper side of disposal container 16 is initially open before assembly, and then, during use, is covered by funnel member 14, and after use, at a suitable time, is covered by top cover 18. Thus, in preparation for use, funnel member 14 is slid onto the disposal container 16 along ridges 20. During the period of use, for convenience and easy accessibility, top cover 18 is slid onto the bottom of the disposal container 16 along ridges 22. This manner of construction places the top cover 18 at a position where it is always convenient and adaptable for immediate access. It is also quite obvious that the ridges and flanges may be oppositely disposed, for example, the ridges may be constructed on the funnel member and the top cover, with the flanges or flange-like indentations placed on the disposal container.

Figure 1A:
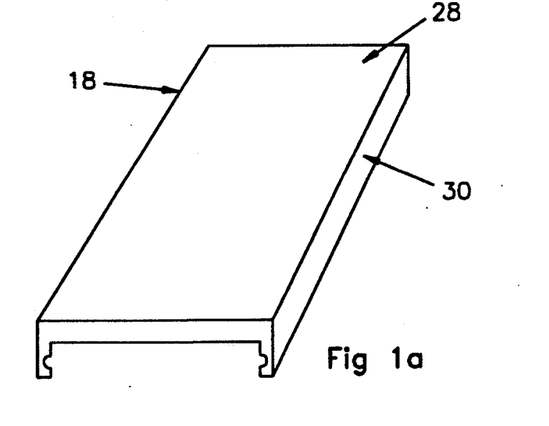
FIG. 1a is a perspective view of a slide-on cover component according to my invention.

FIG. 1a shows the construction of a top cover 18, generally, which comprises the cover portion 28, sides 30, with the flanges 26.

In FIG. 1, the funnel member 14 is shown to include four slanting sides, side portions 32 and end portions 34. The spring-biased door system 12, generally, comprises doors 36 and 38 biased to closed condition by springs 40 and 42 which are connected to the funnel member 14 by connecting springs 44 and 46 and to the doors by connecting pin 48 and 50. The spring-biased doors are biased against door stops 52 installed in position on each end portion 34 of the funnel member 14.

As I mentioned above, the degree of bias given the springs 40 and 42 holding to doors 36 and 38 are chosen so that the doors will open easily when a hypodermic syringe 10, generally, is placed upon the doors to permit the hypodermic syringe 10 to fall into the disposal container 16. I have provided the easy opening and closing of the doors 36 and 38 as one important feature of safety or my device. For example, the door springs may be adjusted to pen the doors is response to the weight of the entire hypodermic syringe 10, generally, or simply in response to he weight of a needle component 54, generally, as shown in FIGS. 4 and 4a including needle-retaining material 56 or 58.

Figure 4:
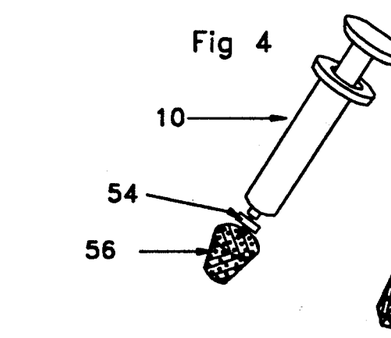
FIG. 4 is a perspective view of one form of needle-retaining material according to my invention in conjunction with a typical hypodermic needle.
Figure 4A:
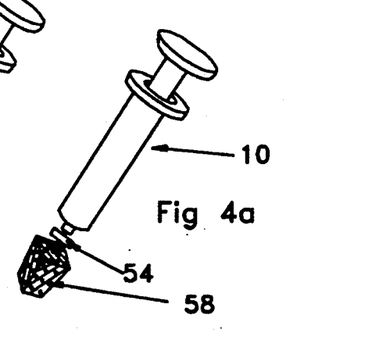
FIG. 4A is a perspective view, similar to FIG. 4, describing a second form of needle-retaining material.

As I describe in FIGS. 4 and 4a, I prefer that the needle retailing components be formed of either conical shape, as shown by FIG. 4, or by pyramidal shape, as shown by FIG. 4a.

In FIGS. 2, 3, 5, and 6, I describe views of two different embodiments of needle receiving trays, as shown by needle receiving tray 60, generally, and needle receiving tray 62, generally.

Figure 2:
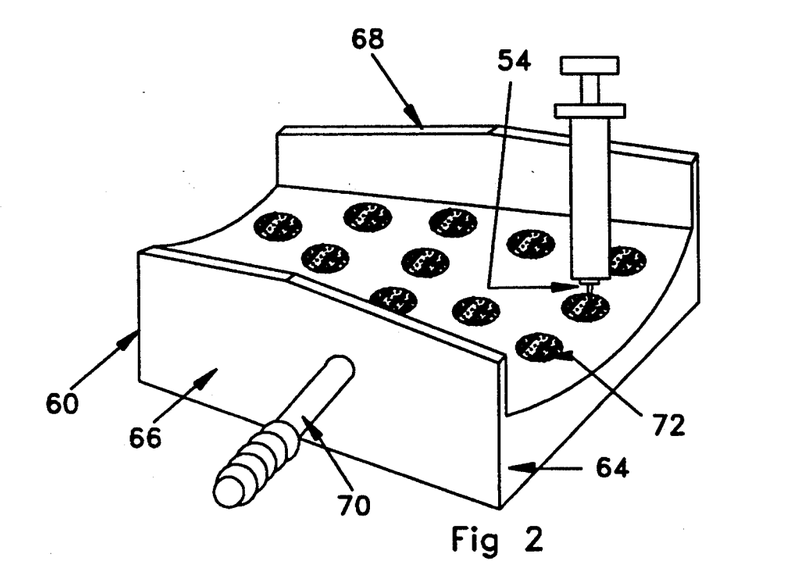
FIG. 2 is a perspective view of one embodiment of a needle collection component according to my invention.
Figure 3:
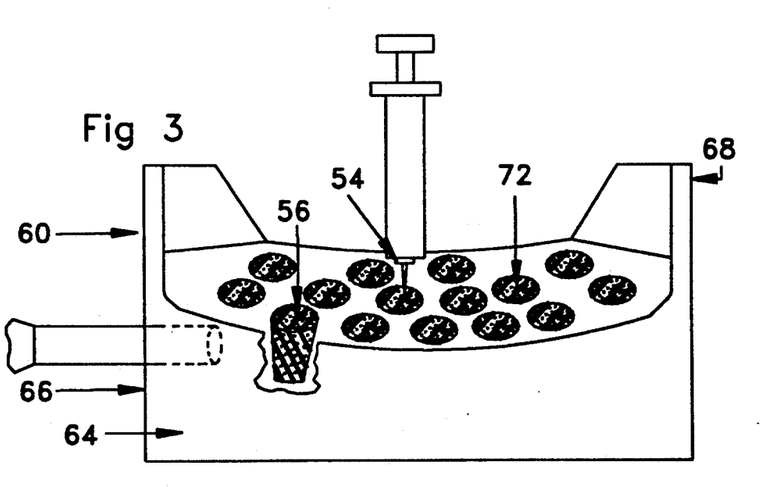
FIG. 3 is a front elevational view, partly in section, of the needle collection component shown in FIG. 2.

In FIGS. 2 and 3, receiving tray 60 comprises a base 64, a pair of side walls 66 and 68, a handle 70 extending outwardly from a side wall, and a plurality of cup-like depressions 72 filled with needle-retaining material. Cup-like depressions 72 should be of the geometric design to conform to the geometry of the needle-retaining material represented by the components 56 or 458 in FIGS. 4 or 4a, whichever would most suitably fit the need at the time. As described above, the geometry o the needle-retaining material is to provide the material with tapered walls so that each unit may be easily removed. receiving tray 62, generally, wherein the tray 62 includes a base 74, a pair of side walls 76 and 78, and a handle 80.

Figure 5:
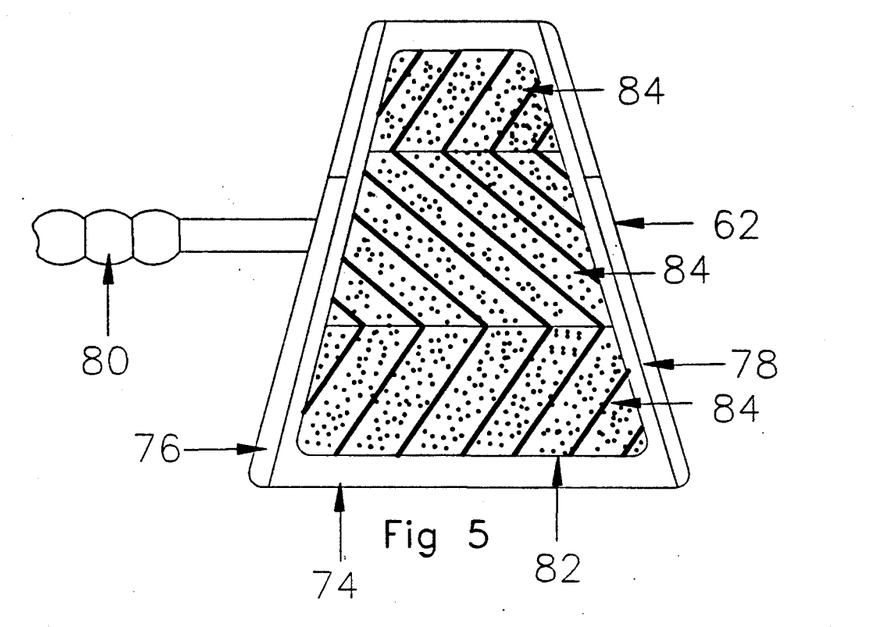
FIG. 5 is a top view of a second embodiment of needle collection component according to my invention.
Figure 6:
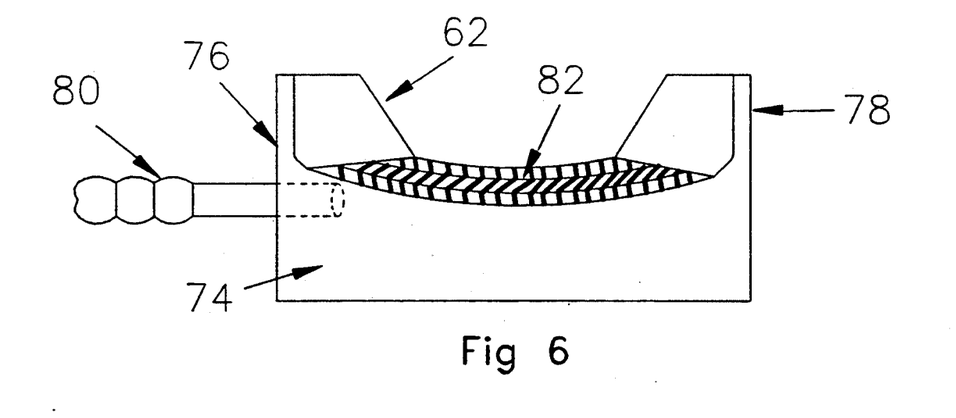
FIG. 6 is a front elevational view of the needle collection component shown in FIG. 5.

Tray 62 is designed to supply the needle-retaining material in wide, contiguous strips filling the tray if the medical technician believes that the condition of the patient requires careful attention, especially when the patient might be erratic. Thus, in this manner the technician may more easily direct a contaminated needle to a larger area than if he or she were allowed to insert the needle into a small area of the needle-retaining material.

Tray 62 includes a large, single depression area 82 which contains a series of strips 84 of needle-retaining material which are preferably continuously arranged in the depression area 82. These strips of needle-retaining material are large enough so that a needle may easily be entered into one or another and a strip may be removed when desired and replaced by a new strip.

Figure 8:
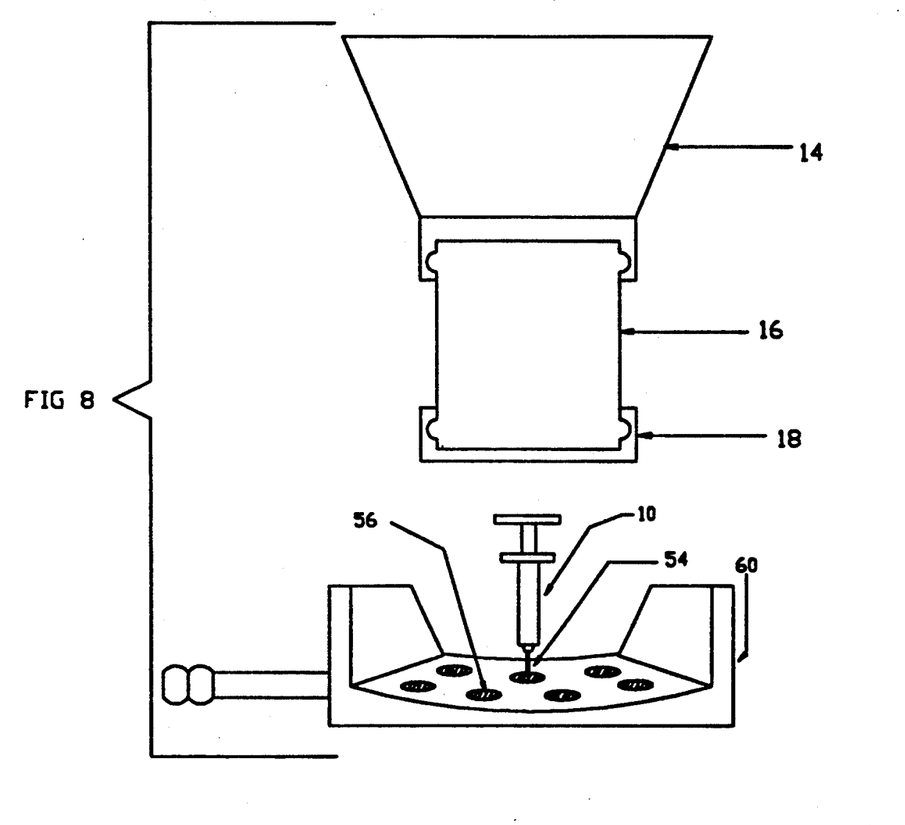
FIG. 8 is an exploded view of one form of a needle disposal system according to my invention.

In FIG. 8, a syringe instrument 10, has been embedded in needle-retaining material 56, as shown in FIG. 4, for deposit upon the door system 12 of the funnel member 14.

Since many different embodiments of my invention may be made without departing from the spirit and scope thereof, it is to be understood that the specific embodiments described in detail herein are not to be taken in a limiting sense, since the scope of the invention is best defined by the appended claims.

I claim:

1. A needle disposal system comprising:
   a tray containing sticky, needle-retaining material adaped to collect contaminated needles inserted therein from a syringe,
   a funnel member having
      an open top portion adapted to receive said needle-retaining material and the inserted contaminated needles from the tray,
      a pair of spring-biased doors which are biased upwardly against a pair of stops on the funnel member,
   a pair of parallel sides,
      a flange member along each of the two parallel sides near the bottom of the funnel member, and
   a disposal container having
      a pair of parallel sides,
      a ridge member along each of the parallel sides near the top of the disposal container, and
   the ridge members of the disposal container being adapted to cooperate with the flange members on the funnel member for slidably positioning the funnel member on the disposal container in order to collect contaminated needles placed upon the doors of the funnel member.

2. A needle disposal system as described in claim 1, which includes
   a top cover member adaptable to cover the disposal container, with the top cover member comprising
   a cover portion,
   a pair of parallel side portions, and
   a flange member along the inside length of each side portion, and
   the disposal container further including
   a ridge along each of the two parallel sides near the bottom of he disposal container adapted to cooperate with the flange members of the top cover member.

3. A needle disposal system as described in claim 2, wherein the bias of the doors is chosen so that the doors will open with the weight of a needle component.

4. A needle disposal system as described in claim 3, wherein the tray includes a plurality of tapered cups each containing needle-retaining material.

5. A needle disposal system as described in claim 3, wherein the tray includes needle-retaining material formed in at least two adjoining strips.

* * * * *

UNITED STATES PATENT AND TRADEMARK OFFICE
CERTIFICATE OF CORRECTION

PATENT NO. : 5,201,418

DATED : April 13, 1993

INVENTOR(S) : Hanlon

It is certified that error appears in the above-identified patent and that said Letters Patent is hereby corrected as shown below:

On the Title page of the patent under [56] U. S. Patent Documents make the following changes:

change patent document No. 3 "Everhardt" to ---Eberhardt---;

change patent document No. 8 "Henifl" to ---Hanifl---;

change patent document No. 10 "Phihon, Sr." to ---Phillion, Sr.--- change patent document No. 18 "Tomes et al" to ---Torres et al---.

Column 1, line 23, change "increase sin" to ---increases in---;

Column 2, line 32, change " drooped " to ---dropped---;

Column 2, line 33, change "he" to ---the---;

Column 2, line 33, change "the paddle wheel" to ---. The paddle wheel---;

Column 2, line 64, change "coinstruments" to ---instruments---;

Column 3, line 16, change "of" to ---for---;

Column 3, line 26, change "fee" to ---free---;

Column 3, line 30, change "eh" to ---the---;

Column 3, line 35, change "onto" to ---not---;

UNITED STATES PATENT AND TRADEMARK OFFICE
CERTIFICATE OF CORRECTION

PATENT NO. : 5,201,418

DATED : April 13, 1993

INVENTOR(S) : Hanlon

It is certified that error appears in the above-identified patent and that said Letters Patent is hereby corrected as shown below:

Column 3, line 39, change "hold feed" to ---should feel---;

Column 3, line 39, change "the" to ---he---;

Column 3, line 50, change "int eh" to ---in the---;

Column 3, line 62, change "eh" to ---the---;

Column 4, line 12, change "o" to ---of---;

Column 4, line 20, change "place din" to ---placed in---;

Column 4, line 27, change "Id" to ---I---;

Column 4, line 33, change "then" to ---than---;

Column 4, line 44, change "here" to ---he or---;

Column 4, line 48, change "IN" to ---In---;

Column 4, line 52, change "he step" to ---the steps --;

Column 4, line 62, change "IN disposable" to ---In disposal---;

Column 4, line 62, change "si" to ---is---;

Column 4, line 64, change "ne" to ---be---;

Column 4, line 67, change "o" to ---to---;

Column 5, line 4, change "apparatus" to ---apparent---;

UNITED STATES PATENT AND TRADEMARK OFFICE
CERTIFICATE OF CORRECTION

PATENT NO. : 5,201,418

DATED : April 13, 1993

INVENTOR(S) : Hanlon

It is certified that error appears in the above-identified patent and that said Letters Patent is hereby corrected as shown below:

Column 5, line 44, change "box-lid" to ---box-like---;

Column 6, line 6, change "springs" to ---pins---;

Column 6, line 11, change "to" to ---the---;

Column 6, line 17, change "or" to ---for---;

Column 6, line 18, change "pen" to ---open---;

Column 6, line 18, change "is" to ---in---;

Column 6, line 20, change "he" to ---the---;

Column 6, line 24, change "retailing" to ---retaining---;

Column 6, line 37, change "458" to ---58---;

Column 6, line 39, change "o" to ---of---;

Signed and Sealed this

First Day of February, 1994

Attest:

BRUCE LEHMAN

Attesting Officer

Commissioner of Patents and Trademarks